(12) United States Patent
Furton et al.

(10) Patent No.: US 9,575,038 B2
(45) Date of Patent: Feb. 21, 2017

(54) UNIVERSAL DETECTOR CALIBRANT

(71) Applicant: THE FLORIDA INTERNATIONAL UNIVERSITY BOARD OF TRUSTEES, Miami, FL (US)

(72) Inventors: Kenneth G. Furton, Miami, FL (US); Katylynn Beltz, Hollywood, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/000,196

(22) Filed: Jan. 19, 2016

(65) Prior Publication Data
US 2016/0131625 A1 May 12, 2016

Related U.S. Application Data

(63) Continuation of application No. 13/400,235, filed on Feb. 20, 2012, now Pat. No. 9,250,222.

(60) Provisional application No. 61/444,430, filed on Feb. 18, 2011.

(51) Int. Cl.
G01N 33/00 (2006.01)
A01K 15/02 (2006.01)
F41H 11/132 (2011.01)

(52) U.S. Cl.
CPC ........... *G01N 33/0006* (2013.01); *A01K 15/02* (2013.01); *F41H 11/132* (2013.01); *G01N 33/0001* (2013.01); *Y10T 436/173845* (2015.01); *Y10T 436/196666* (2015.01)

(58) Field of Classification Search
CPC ...... A01K 15/02; F41H 11/132; G01N 3/0006
USPC .................................. 73/1.01, 1.04
See application file for complete search history.

(56) References Cited

U.S. PATENT DOCUMENTS 9,250,222 B2 2/2016 Furton et al.
2008/0297583 A1 12/2008 Lyons et al.

OTHER PUBLICATIONS

Moulton et al, "The Performance of Dogs in Detecting a-Ionone in the Vapor Phase", 1976, Journal of Comparative Physiology, 110, pp. 287-306.*
Lorenzo et al., "Laboratory and field experiments used to identify *Canis lupus* var. *familiaris* active odor signature chemicals from drugs, explosives, and humans", 2003, Anal Bioanal Chem 376, pp. 1212-1224.*
Beltz et al., Daily reinforcement and determination of detection limits for detection canines through the use of a universal non-target calibration compound(s), Abstract, The Pittsburgh Conference on Analytical Chemistry and Applied Spectroscopy (2010).
(Continued)

*Primary Examiner* — Hezron E Williams
*Assistant Examiner* — David Z Huang
(74) *Attorney, Agent, or Firm* — Marshall, Gerstein & Borun LLP

(57) ABSTRACT

A method of calibrating a biological detector can include training a biological detector to detect a calibration compound, wherein the calibration compound comprises an odor that is detectable by the biological detector and is not used in an environment for which the biological detector is trained to detect odors, presenting the biological detector with a device comprising the calibration compound, and determining whether the biological detector will alert to the calibration compound.

9 Claims, 5 Drawing Sheets

(56) References Cited

OTHER PUBLICATIONS

Beltz et al., The development of a universal non-target calibration compound(s) for the daily reinforcement and determination of detection limits for detection canines, A28, a poster presentation before the 62nd Annual Scientific Meeting of the American Academy of Forensic Sciences (Advance Program), Feb. 22-27, 2010, Seattle, Washington.
Craven et al., Reconstruction and morphometric analysis of the nasal airway of the dog (*Canis familiaris*) and implications regarding olfactory airflow, The Anatomical Record, 290:1325-40 (2007).
Macias, The Development of an Optimized System of Narcotic and Explosive Contraband Mimics for Calibration and Training of Biological Detectors, Dissertation, Florida International University (2009).
Walker et al., Naturalistic quantification of canine olfactory sensitivity, Appl. Animal Behav. Sci., 97(2):241-54 (2006).
Williams et al., Training and maintaining the performance of dogs (*Canis familiaris*) on an increasing numbner of odor discriminations in a controlled setting, Appl. Animal Behaviour Sci., 78:55-65 (2002).

\* cited by examiner

UNIVERSAL DETECTOR CALIBRANT

CROSS-REFERENCE TO RELATED APPLICATION

This application claims the benefit of U.S. Provisional Application No. 61/444,430, filed Feb. 18, 2011, the disclosure of which is incorporated by reference in its entirety.

BACKGROUND

Field of the Disclosure

The disclosure is directed to calibration compounds for calibrating biological detectors and methods for assessing and calibrating biological detectors using the calibration compounds.

Background of Related Technology

Detection canines are widely used in many forensic fields and have been proven to be valuable assets while investigating a case. The use of detection canines is one of the oldest and most reliable means of detection due to the sensitivity of the canine's olfactory system allowing for detection of a wide variety of odors. The use of detection canines as biological detectors is one of the most widely accepted methods for reliable odor detection due to the ability of the canine to quickly and reliable locate the source of an odor to which they are trained. Canines have more than twenty times more olfactory receptors than humans and a nasal anatomy which enables canines to be a highly efficient, sensitive, and selective sample system. However, concern over the validity of canine detection has steadily increased due to the numerous unknowns involved in the mechanism through which canines detect odors. Currently there are no set practices to ensure that biological detectors (e.g., detection canines) are working at a reliable and suitable standard on a daily basis.

SUMMARY OF THE DISCLOSURE

A method of calibrating a biological detector can include training a biological detector to detect a calibration compound, wherein the calibration compound comprises an odor that is detectable by the biological detector and is not used in an environment for which the biological detector is trained to detect odors, presenting the biological detector with a device comprising the calibration compound, and determining whether the biological detector will alert to the calibration compound.

DETAILED DESCRIPTION

Figure 1A:
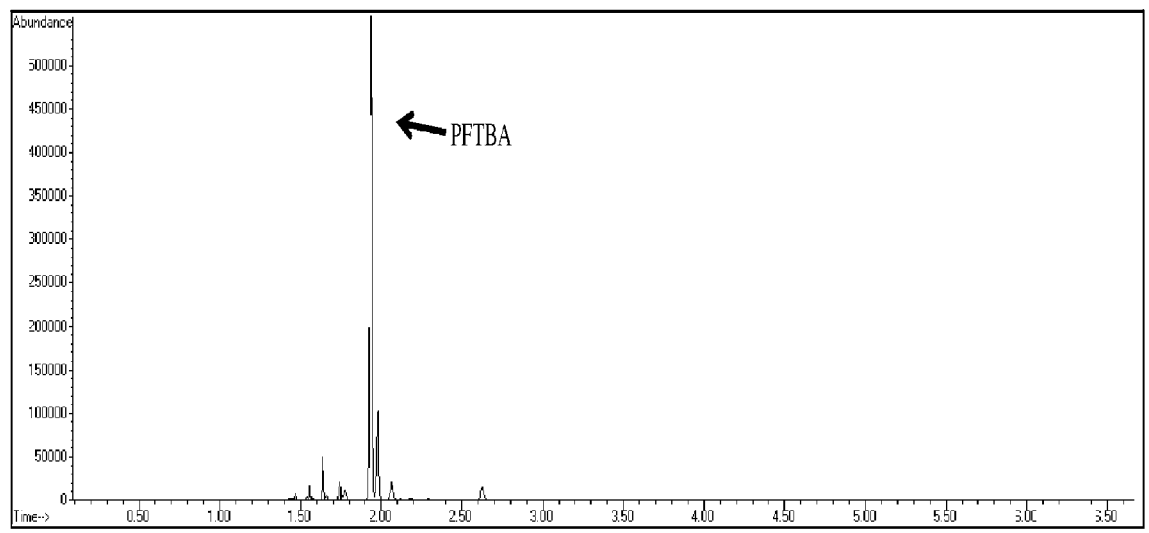
FIGS. 1A-1D are GC/MS spectra of calibration compounds in accordance with an embodiment of the disclosure.
Figure 1B:
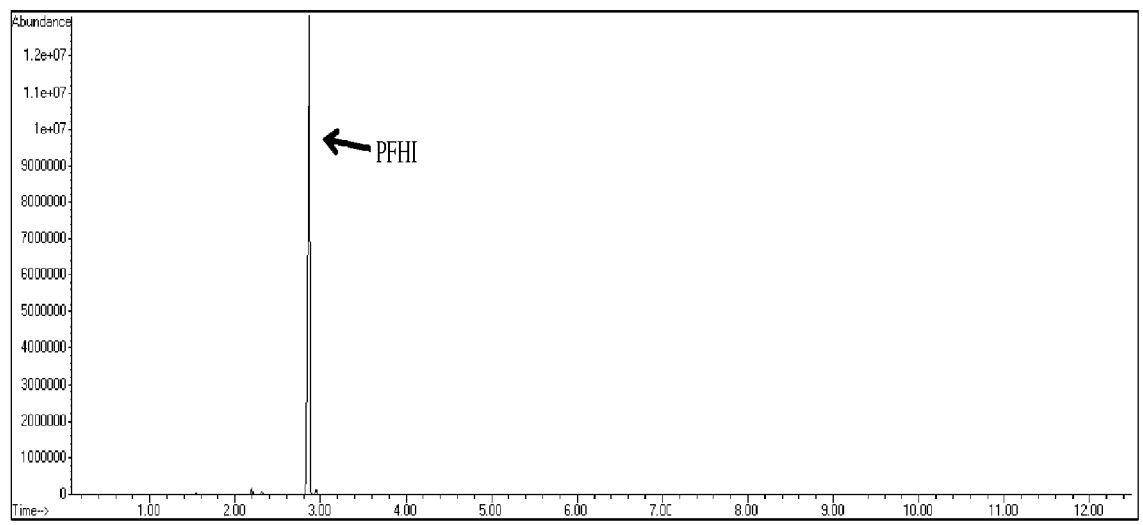
Figure 1C:
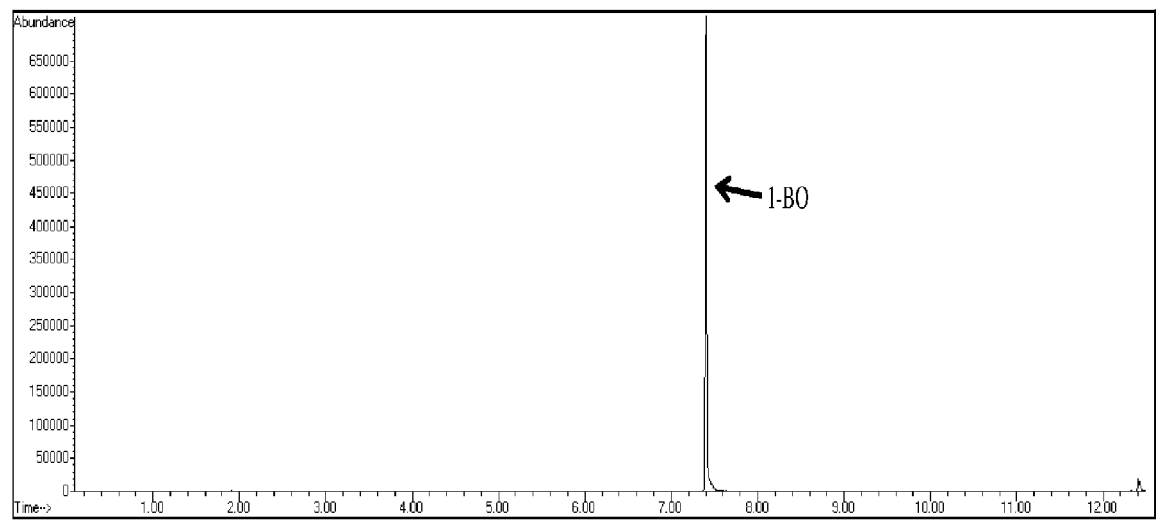
Figure 1D:
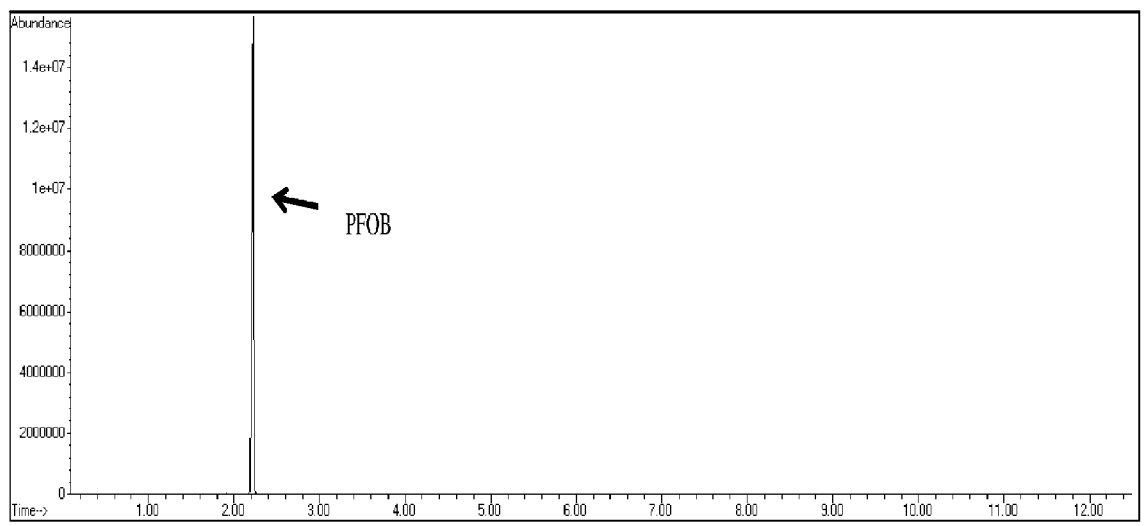

Disclosed herein are calibration compounds for testing the reliability of biological and instrumental detectors and methods of using the calibration compounds. As instruments in a laboratory are calibrated to ensure they are in proper working order, a universal calibration compound for which biological detectors can be calibrated can be useful in verifying the reliability of the biological detector. By testing a biological detector, such as a canine (or more generally, a mammal) using the calibration compound before each working day, a handler can assess and record whether the biological detector is working to suitable standards. Testing using the calibration compound can also be useful as a universal tool for comparing and selecting future biological detectors by determining the time it takes to train the biological detector to alert to the calibration compound and the sensitivity of detection the biological detector can achieve.

As used herein "calibration" refers to the process of determining whether a biological detector properly alerts or detects an odor of a calibration compound and/or measuring the actual quantity of odor the biological detector is detecting, which corresponds to an indicated quantity on the scale of a detection instrument. The biological detector can be, for example, a mammal, or more specifically, a canine. For example, the detection canine can be an explosives, accelerants, narcotics, arson, human scent, or cadaver detecting canine. Other contemplated biological detectors include pigs, rats, bees, and birds. Still other contemplated biological detectors include plants and microorganisms. Contemplated plant detectors include plants that detect odor via a change in color in the presence of a specific odor (e.g., an odor to be detected), such as plants that change color in the presence of TNT. Contemplated microorganism detectors include microorganisms that only grow in the presence of a specific odor, e.g., microorganisms that only grow in the presence of an explosive.

The calibration compounds in accordance with embodiments of the disclosure advantageously satisfy one or more of the following requirements: they pose no danger to the handler or the biological detector, they have no or minimal health hazards, and they are require no special handling or disposal. The calibration compounds are preferably stable and can be used, for example, daily. Stability can be assessed, for example, by storing the compound under elevated humidity (e.g., 45% RH) and temperature (e.g., 50° C.) for prolonged periods of time (e.g., 1 day, 2 days, 4 days, 1 week, 2 weeks, or 1 month) and assessing the degradation of that compound. The compound is stability, for example, if the compound has, e.g., 90% or greater purity, as assessed through, e.g., chromatography or other means for measuring purity. The compound is non-toxic or suitable for daily use, if a biological detector (e.g., dog, rat, pig, bee, or the like) or handler (e.g., human) can be exposed to it at the 10-100× the concentration(s) used in the disclosed methods. Additionally or alternatively, the compound is considered non-toxic or suitable for daily use if the compound has been so designated by a suitable regulatory body.

The compounds preferably have a long halflife, which can ensure that the calibration testing is completed on the parent compound and not a decomposition product. The calibration compounds are preferably thermally stable over a range of temperatures, which advantageously allows the compounds to be used and stored in a variety of climate conditions. The calibration compounds are preferably not widely found in the natural environment, which ensure that the calibration testing is not done with a commonly seen environmental odor. The natural environment can be, for example, the environment in which the biological detector typically works to detect odors (also referred to herein as the "field" or "field environment"). For example, the natural environment of an explosive detecting canine is an environment in which explosives may be located or suspected to be located, such as, for example, an airport or a building.

The calibration compounds are generally non-target odors for biological detectors, which can ensure that there is no cross-detection between classes of biological detectors. For example, it would be disadvantageous for the calibration compound to be an odor commonly detected by explosive detection canines to determine the presence of an explosive because other biological detectors, such as narcotics detection canines would be trained on the calibration compound. Thus, because of the calibration compound training, a narcotics detection canine could alert to the presence of the compound in the field, and the handler would be uncertain as to whether the dog was alerting to a narcotic or an explosive, thereby creating a potentially dangerous situation for the biological detector and the handler and creating further uncertainty as to the detection ability of the odor discriminating canine. In accordance with an embodiment of the disclosure, a method for testing for cross-detection of a potential calibrant compound can include presenting the compound to a odor discriminated canine (for example, an explosive-detecting or a narcotic-detecting canine), previously untrained on the compound. If the odor discriminated canine alerts to the calibration compound, it is likely that the odor is one associated with the class of odors typically detected by the canine.

The calibration compounds of the disclosure are selected such that biological detectors can be trained to detect the odor of the calibration compound. The biological detector must alert to or be trained to alert to the odor of the calibration compound in order to allow for successful calibration testing. Compounds having odors that cannot be differentiated by the biological detectors are not suitable for use as the calibration compound. The compounds must also be sufficiently volatile so that the odor readily becomes present in a gaseous state, making the compound available for detection.

The calibration compounds are preferably readily available so as not to pose specialized manufacturing processes or costs in order to create the calibration compound. Additionally, the calibration compounds preferably have low chemical reactivity so that there are few limitations on the delivery device manufacturing parameters, storage conditions, and testing and training parameters. Chemical reactivity can be tested, for example, by gravimetric and/or gas chromatography/mass spectrometry.

The calibration compounds are preferably suitable for testing the reliability of both biological and instrumental detectors. For example, suitable calibration compounds for use with both biological and instrumental detects can have distinct mass spectral fragmentation patterns to allow for mass spectral detection. If quantifiable instrumental detection is desired, the calibration compound is preferably selected so as to be readily dissolvable in a variety of common solvents.

For quality control, the calibration compound can be detectable by the handler such that the handler can readily determine when the calibration compound has reached the end of its useful life, for example, by detecting a change in the odor emanated by the calibration compound or the lack of odor being emanated.

Thus, disclosed herein are calibration devices for calibrating a biological detector, comprising an absorbent material, a calibration compound applied to the absorbent material, the calibration compound and the absorbent material arranged such that an odor of the calibration compound permeates from the absorbent material; the calibration compound being provided in an amount effective to allow the odor of the calibration compound to be detectable by a biological detector; and the calibration compound being selected such that the calibration compound (1) is not used in an environment in which the biological detector detects odors and (2) is not hazardous to the biological detector. In some cases, the calibration compound is provided such that it is not applied to the absorbent material, but rather is not applied to any material, merely contained within the device. Examples of absorbent materials contemplated include gauze, cellulose, and alumina powder. The calibration device can optionally further comprise a permeable material, such as a polymer bag, wherein the calibration compound (whether applied to an absorbent material or not) is sealed in the permeable material and the odor of the calibration compound can permeate at a constant rate through the permeable material. Specific examples of a permeable material include a polymeric bag or film (e.g., polypropylene, polyethylene, polyacrylate, ethylene-tetrafluoroethylene, fluorinated ethylene propylene, fluorinated high-denisty polyethylene, fluorinated high-density polypropylene, polycarbonate, polyethylene terephyhalate copolyester, perfluoroalkoxy Teflon, polyvinyl chloride, tetrafluoroethylene Teflon, thermoplastic elastomer, or combinations thereof), a non-permeable vessel (e.g., glass) with a lid having a permeable membrane.

In accordance with an embodiment of the disclosure, a method for selecting a calibration compound for calibrating a biological detector can include selecting one or more compounds that pose minimal or no health hazard to the biological detector or a trainer of the biological detector, determining whether the one or more compounds are stable and suitable for daily use, and determining the common environmental uses for the one or more compounds. The one or more compounds are excluded as suitable calibration compounds if they pose a health hazard, are not stable and suitable for daily use, and are commonly found in the environment in which the biological detector works. The method further includes determining whether a biological detector untrained to detect the one or more compounds alerts to the compound as a result of any previous training to detect a dominant odor for which the biological detector is selectively trained (i.e., a narcotics detection canine or an explosive detection canine) and excluding any compounds to which the biological detector alerts. The method also includes determining whether a biological can be trained to alert to the one or more compounds and excluding any compounds to which the biological detector cannot be trained to detect. Any known training method for training a biological detector to alert to an odor can be used.

The method can optionally include excluding as suitable calibration compounds any compound that is not readily available or conveniently prepared.

Calibration compounds can be a halogenated alkyl compound, a halogenated aryl compound, a halogenated vinyl compound, a thiol, an ether, an epoxide, a ketone, an ester, or an aldehyde having the properties noted above, e.g., suitably volatile, having an odor detectable by a biological detector, scarce in the environment, non-toxic to the biological detector, stable. The calibration compound preferably has 1 to 20 carbon atoms and can be linear or branched. In some cases, the calibration compound is halogenated with at least one halogen, and more preferably with two or more halogens. The calibration compound preferably has a vapor pressure of at least $10^{-7}$ mmHg and/or a boiling point of less than 325° C. Specific examples of contemplated calibration compounds include perfluorooctyl bromide (PFOB), 1-bromooctane (1-BO), and perfuloro-n-heptyl iodide (PFHI). Other contemplated calibration compounds include -bromo-2-butene, 2-bromoflourobenzene, N-scetoaceetyl-2-chloroaniline, 3-methyl-1-butanethiol, 1,2-dimethoxybenzene, (+)-trand-limonene 1,2-epoxide, and purine Preferably, the calibration compound includes 1-BO. 1-BO has very limited environmental use and is not commonly encountered in the environments in which detection canines work.

Table 1 below provides a listing of the common environmental uses of several compounds. As shown in Table 1, n-amyl acetate has a variety of environmental uses, which may render it less suitable or unusable as a calibration compound.

TABLE 1

Determination of the Scarcity of the Compound in the Environment

| Compound | Environmental Use | |
|---|---|---|
| n-amyl acetate | Cements and glues | Paper coatings |
| | Lacquers and paints | Leather finishes |
| | Flavoring | Textile sizing and finishes |
| | Perfume | Printing compounds |
| | Nail enamels | Photographic film |
| Perfluorotributylamine (PFTBA) | Mass spectral calibration compound | |
| | Blood substitute | |
| | Cooling agent for small transformers | |
| Perfluorooctyl bromide (PFOB) | Blood substitute | |
| | CT, MR, ultrasounds contrast medium | |
| | Partial liquid ventilation | |
| 1-bromooctane (1-BO) | Solvent used for organic syntheses | |
| Perfluoro-n-heptyl iodide (PFHI) | Organic synthesis reactions | |

The calibration compound preferably permeates at a constant rate either through selection of the compound itself or through the manufacture of the delivery device. Constant permeation rates provide for a standardized delivery device that can reliably and reproducibly permeate a known and selected rate of odor, which can allow for more accurate and reproducible calibration testing results. FIGS. 1A-1D are GC/MS spectra of PFTBA, PFOB, 1-BO, and PFHI.

A suitable calibration compound can be selected, for example, by performing laboratory tests to determine the stability of the compound, to determine if the compound could be detected by common detection instruments (such as GC/MS spectra), and to determine if the compound was capable of permeating and odor at a constant rate. Compounds showing chemical reactivity with a delivery device or one causing corrosion, damage, or discoloration of a surface which it contacted could be excluded as potential calibration compounds. Additionally, compounds that degraded with heat or over time may also be discarded as potential calibration compounds. Optionally, compounds requiring extra processing steps for detection or preparation into delivery devices may also be discarded in favor of compounds that required no additional processing test. Alternatively, such compounds can be selected for use as the calibration compound.

The use of a universal calibration compound as disclosed herein has several advantages for providing a more efficient way to select and train biological detectors. A universal calibration compound can be used to objectively assess a candidate biological detector for ability to detect and alert to a specific odor (i.e., the odor of the universal calibration compound). Because the universal calibration compound is scarce in the environment and has a known concentration, use of the universal calibration compound in assessing the abilities or potential of candidate biological detector provides a trainer objective information about the candidate's detection sensitivity and ability to alert. This assessment of ability of a candidate biological detector is useful regardless of the end detection use of the biological detector (e.g., can be used for biological detectors that are to be trained for detecting accelerants, explosives, drugs, or human remains). Even after selection of the biological detector based upon an objective assessment of their abilities, the universal calibration compound provides a streamlined initial training for the biological detector regardless of end-use (accelerant, drug, explosive, or human remains). To date, the process of training a biological detector is based upon the end-use of that biological detector. However, with a universal calibration compound, the training of the biological detectors is streamlined for initial training. The trainers can begin the training of any biological detector (e.g., on learning search patterns, learning how to alert to an odor, and other general training tasks). Such training is universal to the biological detectors regardless of end use. Moreover, the universal calibration compound can be used throughout the employment of the biological detector as a way to determine continued ability, and sensitivity of the biological detector, as well as for reinforcement training.

A delivery device for the calibration compound can be formed, for example, by directly applying a known quantity of the calibration compound to an absorbent or adsorbent material. For example, a known quantity of the calibration compound can be applied to a sterile gauze pad. The calibration compound is included in the delivery device in an effective amount to be detected by the biological detector. A controlled odor mimic permeation system can also be used as the delivery device. The controlled odor mimic permeation system includes an absorbent or adsorbent material containing a known quantity of the calibration compound that is heat sealed into a permeable polymer bag. The polymer bag controls the rate at which the odor of the calibration compound is permeated to the surrounding area or container. Any other delivery devices known in the art can be used for the calibration compound.

In accordance with an embodiment of the disclosure, a method for testing the reliability of a biological detector using a calibration compound can include first training the biological detector to alert to the calibration compound using any known training techniques for biological detection. The amount of time required to train the biological detectors on the calibration compound can be analyzed to evaluate a biological detectors ability to be trained for detection. This data may be used to determine whether a particular canine is well-suited for training as a biological detector. This testing process can also be used as a standardized method for comparing the aptitude of canines for training as biological detectors (e.g., assessing a candidate biological detector, or more specifically, a candidate canine). This testing process can also be used as a standardized method for comparing the aptitude of different odor discriminating canines for continued use as biological detectors. For example, the training aptitude of a narcotics-trained canine and an explosive-trained canine can be directly compared by testing with the calibration compound. The methods disclosed herein, the, can comprise exposing the candidate canine to a calibration compound and determining if the candidate canine alerts to the calibration compound. If so, the candidate can be deemed likely to succeed in odor detection training, be it for explosives, drugs, accelerants, cadavers or humans. The methods disclosed herein can further comprise exposing the successful candidate canine to an odor compound appropriate for a selected detection end use. For example, the methods can further comprise exposing the biological detector to a narcotics odor for a narcotics detecting canine. Alternatively, the detection odor can be an explosives odor for an explosive detecting canine, an accelerants odor for an arson detecting canine, a human scent for a human detecting canine, or a cadaver odor for a cadaver detecting canine.

Once the biological detector is trained on the calibration compound, the biological detector can be tested, for example, daily, to determine whether the biological detector is properly detecting (or alerting) to the calibration compound. For example, the biological detector can be tested by presenting the biological detector with the calibration compound and determining whether the canine alerts to (i.e., detects) the calibration compound. The calibration compound can be presented in a known amount. For example, the calibration compound can be presented in an amount corresponding to the minimum amount of a compound for which the canine would be considered to be working within suitable standards if the compound is properly detected.

Moreover, the calibration compound can be used as a universal point of comparison of ability two or more biological detectors trained to alter to different detection odors. The use of a standard odor for any biological detector can ensure that the biological detector is working within acceptable sensitivity limits and demonstrate its reliability and robustness.

Additionally, the detection limits of the biological detector can be tested. For example, the detection limits of a biological detector can be tested by presenting the biological detector with varying (and known) amounts of the calibration compound and assessing the lower limit of the amount of the calibration compound to which the biological detector alerts. Such a method can be used as a part of a daily training or field work program to ensure and document that the biological detector is working within acceptable detection limits. Defining the working parameters, such as the detection limits, of the detection canine and evidencing that a detection canine was performing within those limits through testing with the calibration compound can advantageously bolster the reliability of the detection canine's response to specific odors during field use allowing the detection canine's response to withstand greater scrutiny when used, for example, as evidence. The testing method in accordance with embodiments of the disclosure can allow the handler to provide documentation of the canine's functionality based on a standardized testing method using the calibration compound, which can substantiate the handler's claim that the detection canine was working within the acceptable limits when the in-field detection was made.

EXAMPLES

Example 1

1-Bromooctane 1-bromooctane (1-BO) was chosen as the calibration compound. 1-BO is rarely seen in the environment (see Table 1, above) and is safe for daily use. Canines, untrained on the 1-BO compound, were tested to determine if they would alert to the 1-BO compound. With the exception of canine 111, the canines used for the testing were odor discriminating, meaning that these canines will only alert to odors they have been trained on and will not alert to distractor and other odorous materials falling outside the realm of the class of odors the canine has been trained to detect.

The canines were exposed to the 1-BO compound through the use of a controlled odor permeation system. A known amount of the compound was placed on a sterile gauze pad, which was then heat sealed in a 2 ml LDPE bag. The controlled odor permeation system released a known and testable amount of calibration compound. The amount of odor permeating through the bag can be tested by headspace and gravimetric analysis.

Table 2 shows that the tested canines (identified by an identification number) did not alert to the 1-BO compound, indicating that 1-BO is not a dominant odor compound for various classes of detection canines.

TABLE 2

Odor Recognition Test Before Training

| Class of Detection Canine | Alert (%) | Interest (%) | No Alert (%) |
|---|---|---|---|
| Explosives (n = 22) | — | 9* | 86 |
| Drug (n = 13) | — | — | 100 |
| Accelerant (n = 2) | — | — | 100 |

*Canine is not odor discriminating

The canines were then trained to alert to the 1-BO calibration compound. Table 3 demonstrates that the detection canines were successfully trained to alert to the 1-BO calibration compound.

TABLE 3

Odor Recognition Test After Training

| Class of Detection Canine | Successfully Imprinted | Unsuccessfully Imprinted |
|---|---|---|
| Explosives (n = 5) | 100% | |
| Drug (n = 3) | 100% | |

Figure 2:
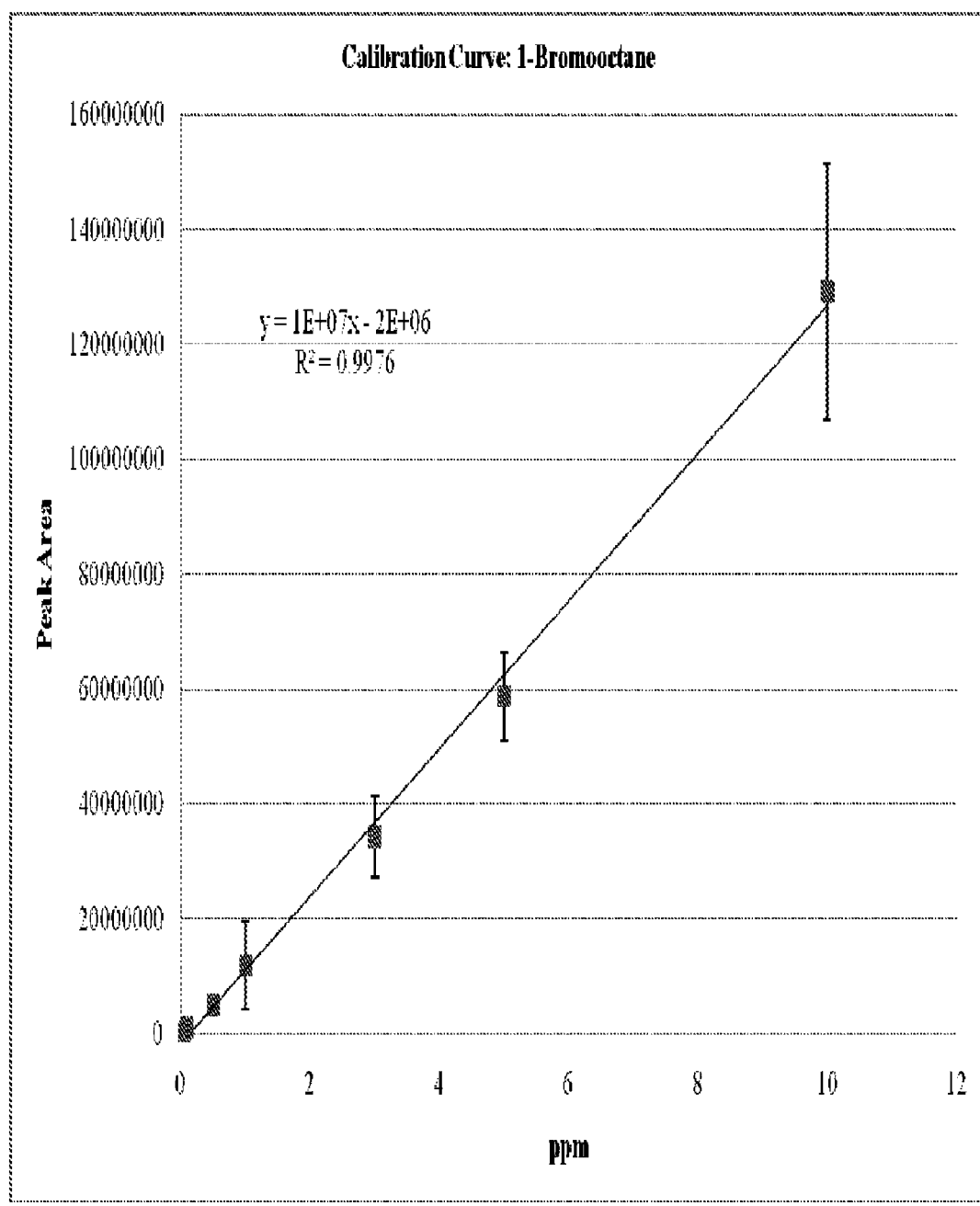
FIG. 2 is a graph of the calibration curve of 1-bromooctane.

1-BO is also readily detectable instrumentally and has the potential to be used as an instrumental calibrant in a variety of instrumental detectors because it has a distinct mass spectral fragmentation pattern. FIG. 2 shows a calibration curve of 1-BO performed on a GC/MS instrument.

Example 2

Perfluorotributylamine (PFTBA)

Perfluorotributylamine (PFTBA) was tested as a calibration compound to determine whether detection canines could be successfully trained to alert to the calibration compound. Samples of PFTBA were supplied to a local dog trainer and incorporated into the training regimen of two canines (identified as nos. 136 and 143). The training consisted of three days of presentation and imprint using the calibration compound in accordance with known detection training standards and conducted by a veteran, IFRI certified canine trainer.

After successful imprint, a PFTBA sample and blank sample were presented to the canines in a double-blind fashion. The target odors were prepared by applying PFTBA to a sterile piece of gauze and heat sealing the gauze in a 3 in by 3 in, 2 ml LDPE bag. The blank sample consisted of a piece of gauze heat sealed within the LDPE bag. Both samples were hidden between rows of boxes similar to a typical training scenario. The handlers were instructed to walk their canines in a typical search pattern and identify the canine's response as "alert", "no alert", or "interest." Table 4 provides the results of the testing.

TABLE 4

| | Field Testing with PFTBA Training | | | |
|---|---|---|---|---|
| Content | No Alert | Interest | Alert | % Alert |
| PFTBA | — | — | 136, 143 | 100% |
| Blank | 136, 143 | — | — | 0% |

Both canines correctly identified and altered to the PFTBA sample without falsely alerting to the blank sample. While the training sequence for detecting the PFTBA calibration compound was shorter than accepted training regimens by most agencies, the canines had no trouble imprinting upon the odor of the sample. Accordingly, the PFTBA proved suitable for use as a calibration compound for canine detectors.

Although the foregoing text is a detailed description of numerous different embodiments of an ink formulation in accordance with the disclosure, the detailed description is to be construed as exemplary only and does not describe every possible embodiment of in accordance with the disclosure. Consequently only such limitations as appear in the appended claims should be placed on the invention.

What is claimed:

1. A method of calibrating a biological detector, comprising:
    training a biological detector to detect a calibration compound, wherein the calibration compound comprises an odor that is detectable by the biological detector and is not used in an environment for which the biological detector is trained to detect odors;
    presenting the biological detector with a device comprising the calibration compound; and
    determining whether the biological detector will alert to the calibration compound,
    wherein the calibration compound is selected from the group consisting of perfluorooctyl bromide (PFOB), 1-bromooctane (1-BO), perfluoro-n-heptyl iodide (PFHI), bromo-2-butene, 2-bromofluorobenzene, N-acetoacetyl-2-chloroaniline, 3-methyl-1-butanethiol, 1,2-dimethoxybenzene, (+)-trans-limonene 1,2-epoxide, and purine.

2. The method of claim 1, wherein the biological detector is an odor discriminating biological detector.

3. The method of claim 1, wherein the biological detector is an explosive detecting canine, a narcotic detecting canine, an arson detecting canine, a human scent detecting canine, or a cadaver detecting canine.

4. A method of determining the detection limit of a biological detector, comprising:
    presenting a biological detector with a line-up of calibration devices, each calibration device comprising a predetermined amount of a calibration compound, wherein each calibration device comprises different amounts of the calibration compound, the biological detector is pre-trained to detect the calibration compound, and wherein the calibration compound is not found in an environment for which the biological detector is trained to detect odors; and
    determining the lowest amount of the calibration compound to which the biological detector will alert,
    wherein the calibration compound is selected from the group consisting of perfluorooctyl bromide (PFOB), 1-bromooctane (1-BO), perfluoro-n-heptyl iodide (PFHI), bromo-2-butene, 2-bromofluorobenzene, N-acetoacetyl-2-chloroaniline, 3-methyl-1-butanethiol, 1,2-dimethoxybenzene, (+)-trans-limonene 1,2-epoxide, and purine.

5. The method of claim 4, wherein the biological detector is an odor discriminating biological detector.

6. The method of claim 4, wherein the biological detector is a narcotics detecting canine, an explosive detecting canine, an arson detecting canine, a human scent detecting canine, or a cadaver detecting canine.

7. A method to assess a biological detector comprising
    exposing the biological detector to a calibration compound, wherein the calibration compound comprises a halogenated alkyl compound, a halogenated aryl compound, a halogenated vinyl compound, a thiol, an ether, an epoxide, a ketone, an ester, or an aldehyde; and
    determining whether the biological detector alerts to the calibration compound,
    wherein the calibration compound is selected from the group consisting of perfluorooctyl bromide (PFOB), 1-bromooctane (1-BO), perfluoro-n-heptyl iodide (PFHI), bromo-2-butene, 2-bromofluorobenzene, N-acetoacetyl-2-chloroaniline, 3-methyl-1-butanethiol, 1,2-dimethoxybenzene, (+)-trans-limonene 1,2-epoxide, and purine.

8. The method of claim 7, further comprising exposing the biological detector to a detection odor.

9. The method of claim 8, wherein the biological detector is (a) a narcotics detecting canine and the detection odor is a narcotics odor; (b) an accelerant detecting canine and the detection odor is an accelerant odor; (c) an explosives detecting canine and the detection odor is an explosives odor; or (d) a cadaver detecting canine and the detection odor is a cadaver odor.

* * * * *